United States Patent [19]

Andersen

[11] Patent Number: 4,580,564

[45] Date of Patent: Apr. 8, 1986

[54] FINGER PRICKING DEVICE

[76] Inventor: Michael A. Andersen, 5307 S. Harding Ave., Chicago, Ill. 60632

[21] Appl. No.: 502,008

[22] Filed: Jun. 7, 1983

[51] Int. Cl.<sup>4</sup> ............................................. A61B 17/32
[52] U.S. Cl. ................................. 128/314; 128/329 R
[58] Field of Search .................. 128/314, 315, 329 R, 128/333

[56] References Cited

U.S. PATENT DOCUMENTS

| | | | |
|---|---|---|---|
| 4,230,118 | 10/1980 | Holman et al. | 128/314 |
| 4,399,456 | 4/1983 | Cornell et al. | 128/314 |
| 4,416,279 | 11/1983 | Lindner et al. | 128/314 |
| 4,462,405 | 7/1984 | Ehrlich | 128/329 R |

FOREIGN PATENT DOCUMENTS

| | | | |
|---|---|---|---|
| 188439 | 1/1957 | Fed. Rep. of Germany | 128/314 |
| 1133137 | 3/1957 | France | 128/314 |

OTHER PUBLICATIONS

"New Tests to Monitor Diabetes at Home" from *Consumer Reports*, Jun., 1982 pp. 318–320.
"Home Glucose Monitoring Becomes More Sophisticated", from *Contemporory Ob/Gyn Technology*, 1983, pp. 7–9 and 12, 14.
"Autolet" by Owen Mumford Ltd., *Medical Division*, Published by Owen Mumford Ltd. 1981.

*Primary Examiner*—C. Fred Rosenbaum
*Assistant Examiner*—Gene B. Kartchner
*Attorney, Agent, or Firm*—Willian Brinks Olds Hofer Gilson & Lione Ltd.

[57] ABSTRACT

A finger pricking apparatus is disclosed which includes a stop, a guide, a weight and a lancet. The lancet comprises a base, a handle and a needle. The needle is disposed centrally within the base and the handle such that it protrudes from the handle. The lancet is seated in a recess defined by the weight. The weight and lancet are free to reciprocate in the guide. The guide defines a first end and a second end. The stop is seated in the first end of the guide. The stop cooperates with the weight to control depth of puncture of the lancet. In use, the weighted lancet is loaded into the guide. The guide is held between two fingers and inverted. The weighted lancet is thereby caused to travel from the first end to the second end of the guide. When it reaches the first end, the weight contacts the stop, preventing further movement of the lancet. The needle of the lancet protrudes through an opening defined by the stop and pierces a finger, thereby allowing a drop of blood to be drawn.

14 Claims, 8 Drawing Figures

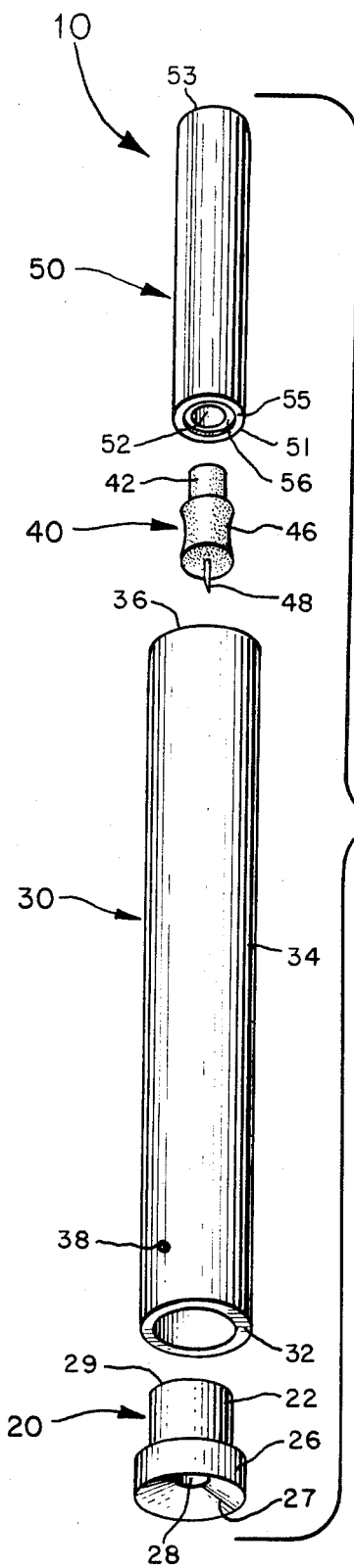
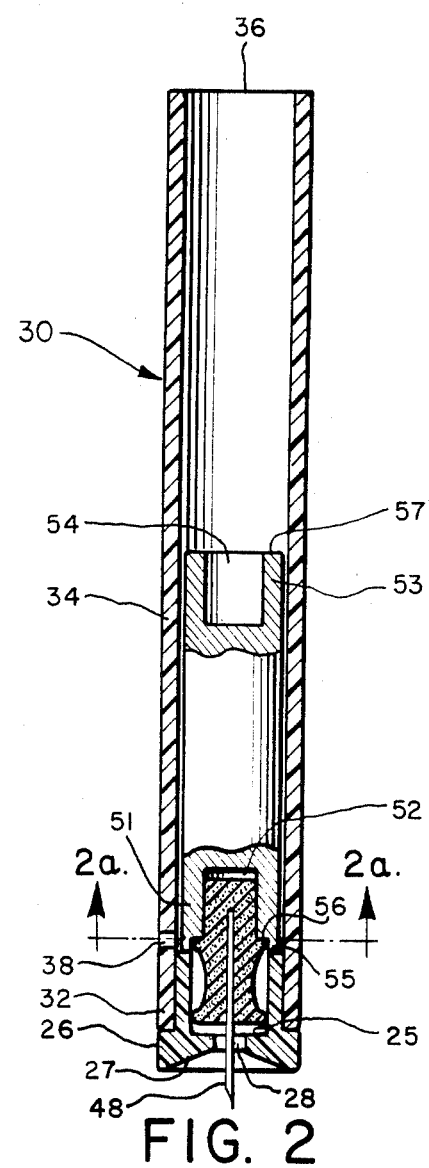
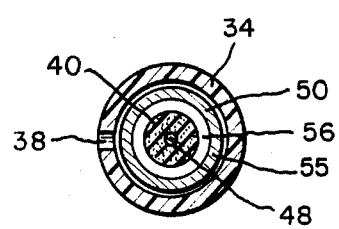

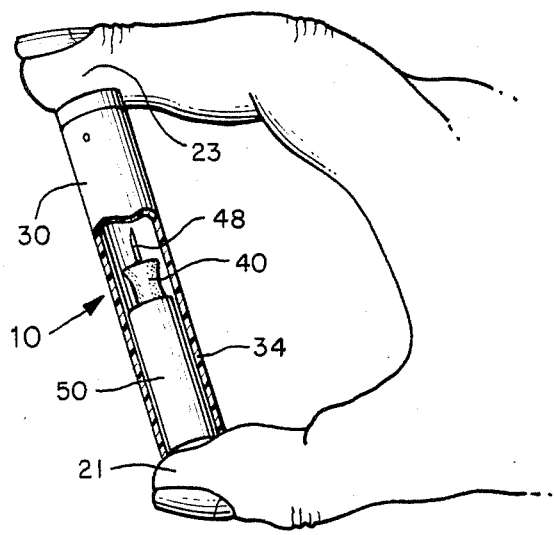
FIG. 3a
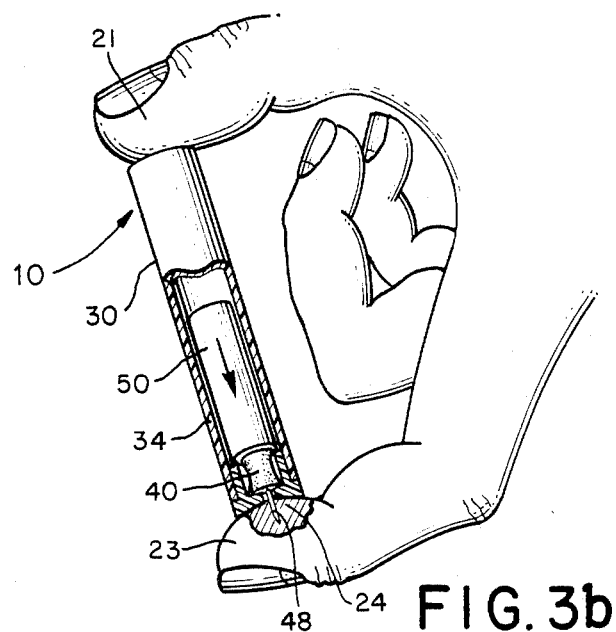
FIG. 3b
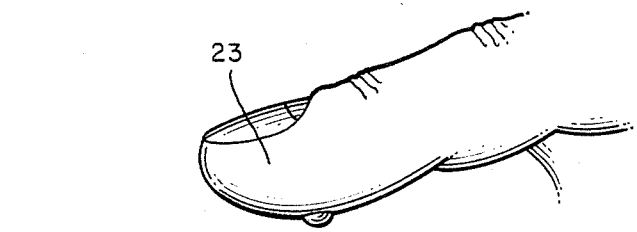
FIG. 3c
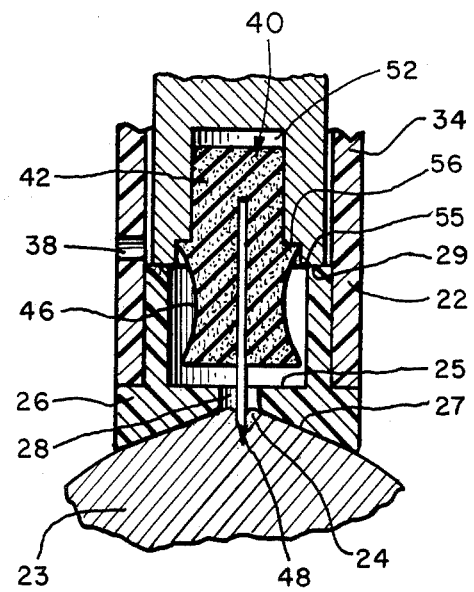
FIG. 4a
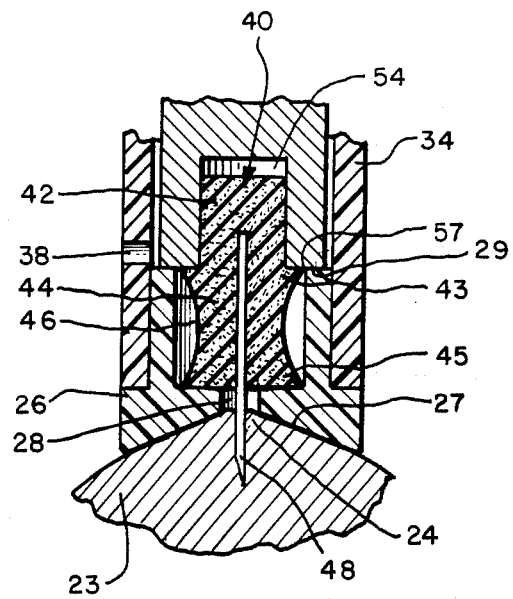
FIG. 4b

FINGER PRICKING DEVICE

BACKGROUND OF THE INVENTION

This invention relates to an apparatus for drawing a drop of blood, especially from a person's finger. The apparatus is designed primarily for use in a home monitoring program.

In the past, patients such as diabetics on home monitoring programs faced a daily trauma of extracting blood by jabbing a finger with a lancet. This chore was accompanied by considerable anticipation of agony—an anticipation often fulfilled. Attempts to resolve the problem by providing spring loaded finger pricking mechanisms which must be cocked and released are not without drawbacks.

First, these spring loaded trigger mechanisms tend to be of relatively complex construction. These mechanisms are operated by cocking a spring which is in cooperation with a lancet, latching the spring, and then releasing it. The working order of the mechanism is limited by that of the spring, the latch, and any other parts incorporated therein.

Further, complex spring mechanisms translate into high initial costs for consumers, in addition to potential replacement costs resulting from worn out parts. An although attempts have been made to simplify spring mechanisms to curb consumer costs, these attempts have failed to yield a product which is non-traumatic (i.e. not emotionally stressful) to use as well as inexpensive.

Thus, there presently exists a need for a finger pricking apparatus which is simple, quick and nontraumatic to use, and simple to construct, and there exists a need for an efficient method of use for such an apparatus. There also exists a need for a convenient method for adjusting needle penetration.

SUMMARY OF THE INVENTION

An important object of the present invention is to provide an improved finger pricking apparatus which is simple and inexpensive to construct. According to this aspect of the invention, an apparatus is provided which comprises a guide having a first end and a second end, a lancet and a weight. A stop may also be incorporated into the apparatus at the first end of the guide. The parts are ideally of very simple construction, and except for the lancet, they will not wear out with use.

A further object of the invention is to provide an improved finger pricking apparatus which is quick and simple to use. According to this aspect of the invention, an apparatus is provided which need only be manipulated between a first and a second finger, placed respectively over the first and second ends of the guide, for example by inverting the guide.

Yet another object of the invention is to teach a simple and efficient method of using the finger pricking apparatus of the present invention. According to this aspect of the invention, the method consists of inserting a weighted lancet into a guide having first and second ends, at the second end; holding the guide between a first finger (preferably, the first finger is a forefinger) at the first end and a second finger (preferably the second finger is a thumb) at the second end, such that the first end of the guide is disposed at a higher level than the second end of the guide; and then manipulating the guide such that second end is disposed at a higher level than the first end. Henceforth the process of manipulating the guide in this manner will be referred to as "inverting the guide". In this manner, the weighted lancet is caused to travel from the second end to the first end of the guide. Upon reaching the second end, the lancet pierces the first finger, thereby allowing a drop of blood to be drawn. The entire procedure can be accomplished in a second or two.

A still further object of the invention is to provide an improved lancet which may be adjusted in the apparatus to pierce the first finger at a selected depth.

The presently preferred embodiment of this invention described below provides a number of important advantages. The guide is of extremely simple construction. Its opacity removes much trauma from the finger pricking procedure, for the lancet cannot be seen as it travels through the guide. The stop inserted at the first end of the guide acts in cooperation with a lower rim of the weight to control depth of puncture of the lancet by ensuring optimal placement of the lancet as it pierces the first finger.

The finger pricking apparatus of this invention has been found to facilitate quick, simple, and nontraumatic piercing of the finger. These factors make it suitable for use by children as well as adults. Further, its simplicity of construction will insure to the benefit of consumers of all ages.

The invention itself, together with further objects and attendant advantages, will best be understood by reference to the following detailed description taken in conjunction with the accompanying drawings.

BRIEF DESCRIPTION OF DRAWINGS

FIG. 1 is an exploded perspective view of a presently preferred embodiment of the finger pricking apparatus of the present invention.

FIG. 2 is a cross sectional view of the apparatus of FIG. 1.

FIG. 2a is a cross-sectional view of the apparatus of FIG. 1, taken along the line 2a—2a of FIG. 2.

FIGS. 3a, b, and c together show a preferred embodiment of the method of the present invention utilizing the embodiment of FIG. 1.

FIGS. 4a and b together show the adjustable weighted lancet of FIG. 1 in two separate orientations.

DETAILED DESCRIPTION OF THE PRESENTLY PREFERRED EMBODIMENTS

Turning now to the drawings, FIGS. 1 through 4a and b show various views of the presently preferred embodiment of the finger pricking apparatus 10 and the method of this invention. As shown in FIGS. 1 and 2, this finger pricking apparatus 10 includes a stop 20, a rigid cylindrical guide 30, a lancet 40 and a weight 50.

In the presently preferred embodiment of the invention, the stop 20 is seated in a first end 32 of the rigid cylindrical guide 30. This is accomplished by constructing the stop 20 to define a cylindrical tube 22 adapted to fit snugly within the first end 32 of the rigid cylindrical guide 30. The cylindrical tube 22 defines a stop surface 29. The stop 20 may optionally be secured at the cylindrical tube 22, by a suitable adhesive, to the guide 30 at the first end 32. However, the stop 20 is not secured to the guide 30 in the preferred embodiment, because cleaning of the apparatus 10 is facilitated by removability of the stop 20.

The stop 20 of the preferred embodiment as best seen in FIGS. 1, 2 and 4 further defines a platform 26, having a central opening 28, an inner surface 25, and an outer surface 27. In use, the outer surface 27 is placed against a first finger 23. The central opening 28 causes a dimple of skin 24 to form on the first finger 23, and thereby facilitates the piercing operation.

The rigid cylindrical guide 30 of the preferred embodiment simply defines a tubular shell 34 having a first end 32 and a second end 36. The shell 34 is opaque in the preferred embodiment in order to minimize any trauma associated with the finger pricking operation. In the preferred embodiment the shell 34 defines an orifice 38 suitable for avoiding an air cushion build up when the finger pricking apparatus 10 is in use. However, air cushion build up may also be avoided by constructing a weight 50 defining grooves along its length, or by constructing flutes along inside length of cylindrical guide 30.

The lancet 40 and weight 50 are best shown in FIGS. 4a and b. The lancet 40 comprises a cylindrical base 42 defining a uniform cross-sectional width. The base 42 further defines a handle 44 having an external shoulder 43, a flat outer end 45 and a concave arcuate surface 46. A needle 48 is disposed centrally within the handle 44 and protrudes from the flat end 45 of the handle 44. The handle 44 facilitates the adjustment described below of the lancet 40 in the weight 50.

The weight 50 defines a first end 51 and a second end 53. The weight 50 is constructed in a cylindrical shape such that it is of marginally smaller diameter than the shell 34. The weight 50 should be free to reciprocate within the shell 34. If the shell 34 does not define an air vent orifice 38, then the weight 50 may define grooves running from the first end 51 to the second end 53 of the weight, or cylindrical 30 may define flutes running from the end 32 to the end 36 of the cylinder. The weight 50 defines at least one recess 52 at the first end 51. The weight 50 of the presently preferred embodiment also defines a second recess 54 at the second end 53. The weight 50 further defines a first lower rim 55 and an internal shoulder 56 at the first end 51, and a second lower rim 57 at the second end 53. When shallow needle penetration is desired, the base 42 of the lancet 40 is seated in the first recess 52 such that the external shoulder 43 of the handle 44 is seated on the internal shoulder 56 of the weight 50. When deeper needle penetration is desired, the base 42 of the lancet 40 is seated in the second recess 54 such that the external shoulder 43 of the handle 44 bears against the second lower rim 57 of the weight 50. The lancet 40 is held in place by friction between the base 42 and the first recess 52 or the second recess 54.

In use, the weighted lancet 40 passes along the guide 30 from the second end 36 to the first end 32. At the first end 32, the first lower rim 55 or the second lower rim 57 of the weight 50 engages with the stop surface 29 of the stop 20, while the needle 48 of the lancet 40 protrudes through the central opening 28 defined by the platform 26. When the lancet 40 is seated in the first recess 52 such that the base 42 fits snugly in the first recess 52 and the external shoulder 43 of the handle 44 bears against the internal shoulder 56 of the weight 50, the first lower rim 55 will come into contact with the stop surface 29 of the stop 20, such that depth of penetration of the needle 48 will occur at a first level. When the lancet 40 is seated in the second recess 54 such that the base 42 fits snugly in the second recess 54 and the external shoulder 43 of the handle 44 bears against the second lower rim 57 of the weight 50, the second lower rim 57 will come into contact with the stop surface 29 of the stop 20, such that depth of penetration of the needle 48 will occur at a second level. The second level is deeper than the first level.

Alternatively, the lancet 40 may be of the standard disposable type available on the market today such as the Autoclix lancet (available from Bio-Dynamics, Indianapolis, Indiana). These lancets comprise a needle and a base. The base has a first end, a second end and a cross-shaped cross-section. It is constructed of resilient elastomeric material and may be placed in the first recess 52 or the second recess 54 defined by the weight 50. The base is held in place by friction. The needle is disposed centrally within the base and protrudes from the second end of the base.

The following dimensions are illustrative for the presently preferred embodiment. The platform 27 defined by the stop 20 has a thickness of about one eighth of an inch, measured as the greatest distance between the inner surface 25 and the outer surface 26 of the platform 26. The cylindrical tube 22 defined by the stop is about five sixteenths of an inch in length. The tube 22 has an outer diameter about the same size or marginally smaller than the inner diameter of the shell 34, which is seven sixteenths of an inch. The length of the shell 34 is about three and five eighths inches. The length of the lancet 40 is about one half inch: three sixteenths of an inch for the base 42 and five sixteenths of an inch for the handle 44. The cylindrical base 42 has a diameter of three sixteenths of an inch. The handle 44 has a diameter of five sixteenths of an inch when measured at the external shoulder 43 or at the flat end 45, and a diameter of three sixteenths of an inch when measured at the narrowest part of the concave arcuate surface 46. The needle 48 protrudes at least one eighth of an inch from the handle 44. The length of the weight 50 is about one and one half inches and its diameter is about or marginally less then seven sixteenths of an inch. The recesses 52 and 54 defined by the weight 50 have a diameter of about three sixteenths of an inch (one quarter of an inch when standard lancets are used). The depth of the first recess 52 when measured to the internal shoulder 56 is seven thirty-seconds of an inch, and the distance from the internal shoulder 56 to the first lower rim 55 is one thirty-second of an inch. The depth of the second recess 54 when measured to the second lower rim 57 is seven thirty-seconds of an inch. The first lower rim 55 has a width of one sixteenth of an inch and the second lower rim 57 has a width of one eighth of an inch. The platform 20 is ideally constructed of a flexible plastic material. The cylindrical guide 30 is constructed of a rigid opaque plastic, preferably in a bright or attractive color. The weight is preferably constructed from a stainless steel.

Having described the structure of the preferred embodiments, the preferred method of operation can now be described in detail. The preferred method of use involves seating the base 42 of a sterile lancet 40 in the first recess 52 or the second recess 54 defined by the weight 50, such that the external shoulder 43 of the handle 44 bears against the internal shoulder 56 or the second lower rim 57 respectively; loading the weighted lancet 40 into the cylindrical guide 30 at the second end 36 while the first end 32 is positioned at a higher level than the second end 36; covering the second end 36 with a thumb 21 and covering the outer surface 27 of the platform 26 adjacent the first end 32 with a forefinger 23; and inverting the apparatus 10 such that the first end 32 is positioned at a lower level than the second end 36 at the completion of the operation. This will result in the motion of the weighted lancet 40 from the second end 36 to the first end 32 of the cylindrical guide 30. At the first end 32, the first lower rim 55 or the second lower rim 57 of the weight 50 will come into contact with the stop surface 29 defined by the cylindrical tube 22 of the stop 20. The needle 48 of the lancet 40 will protrude from the opening 28 defined by the platform 26, and the needle will thereupon prick the forefinger 23 covering the outer surface 27 defined by the platform 26, thereby allowing a drop of blood to be drawn.

One of the important advantages of this invention is that the method of operation is extremely simple: for example, springs do not have to be reset prior to each use. Hence, the entire operation of the present invention can, in most cases, be independently carried out by young children. Also, the entire operation can be completed in a few seconds.

A further advantage is that the construction of the apparatus is simple. This aspect of the invention actually encompasses two sub-advantages. First, the apparatus may be manufactured inexpensively, so that it may be offered to consumers at a comparatively low price. Second, the apparatus is highly durable. There should rarely, if ever, be a need for replacement parts (except for the lancet).

A still further advantage is that the method is non-traumatic. The needle of the lancet is not seen as it pierces the skin. Also, a simple movement of the fingers accomplishes the finger pricking task. There should be less trauma associated with the present method than with the cocked spring and trigger methods, because here there is not the sense of "shooting" one's self by pulling a trigger. In summary, this invention provides a quick and efficient apparatus for drawing blood which is inexpensive to construct, highly durable, and simple and non-traumatic to use.

It should be understood that the present invention is not limited to the precise structure described above. Rather, a wide range of modifications can be made to this finger pricking apparatus and method without departing from the spirit of this invention. For example, an open U-shaped guide can be used to guide the movement of a weighted lancet from a first end of the guide to a second end.

Thus, a wide variety of shapes and arrangements can be adapted for use with this invention. In addition, changes to materials, details of construction and dimensions can be made to the preferred embodiment described above. For example, the lancet itself can define a stop to control depth of piercing; the stop need not be provided as a separate part of the apparatus. It is therefore intended that the foregoing detailed description be regarded as illustrative rather than limiting, and that it be understood that it is the following claims, including all equivalents, which are intended to define the scope of this invention.

I claim:

1. An apparatus for drawing blood comprising:
   a guide having a first end and a second end; and
   a weighted lancet having a selected mass no less than about 0.9 oz. and comprising a needle at one end positioned to protrude from the first end of said guide;
   said guide having a length greater than that of said weighted lancet;
   said weighted lancet mounted to slide freely in said guide without constraint through a selected distance;
   said selected mass and said selected distance selected such that, when said said guide is inverted with a finger adjacent the first end, inertial forces alone acting on said weighted lancet in free fall develop sufficient momentum to force the needle out of the first end and to puncture the finger, thereby drawing a drop of blood from the finger.

2. The apparatus of claim 1 wherein said guide is constructed of an opaque material.

3. The apparatus of claim 1 wherein said guide comprises a tubular shell sized to receive said weighted lancet.

4. The apparatus of claim 1 further comprising a stop mounted to said guide to control depth of puncture by said lancet.

5. The apparatus of claim 4 wherein said stop comprises a platform defining a central opening, a stop surface and an outer surface, such that the central opening may be placed adjacent to an area of skin to be punctured to cause the outer surface to bear against said finger, and the stop surface to bear against a portion of said weighted lancet, thereby controlling depth of puncture.

6. The apparatus of claim 3 wherein said weighted lancet comprises:
   a cylindrical weight defining a first end, a second end, and a first recess at the first end; and
   a lancet including a base shaped to fit in the first recess, wherein the needle is disposed centrally to the base such that it projects from the base.

7. The apparatus of claim 6 wherein said weight further defines a second recess at the second end, and wherein the second recess is also shaped to receive the base.

8. An apparatus for drawing blood comprising:
   a cylindrical guide comprising a tubular shell, said shell defining a first end, a second end, and an opaque surface;
   a metal weight received within the tubular shell and freely slidable therein through a selected distance, said weight defining first and second ends and a recess in the first end;
   a stop comprising a tubular portion nested within the first end of said cylindrical guide, and a platform which extends across the first end, said platform defining an outer surface and a central opening; and
   a lancet which comprises a base received in the recess, said lancet positioned to extend out of said cylindrical guide through the central opening;
   said weight and lancet defining a combined mass;
   said combined mass and said selected distance selected such that when said guide is inverted, inertial forces alone acting on said weight and lancet accelerate said weight and the lancet in free fall through the selected distance to generate a sufficient momentum in said weight and lancet to drive said lancet through the central opening to pierce a finger adjacent the outer surface to draw a drop of blood from the finger.

9. The apparatus of claim 8, wherein the tubular shell further defines an air vent orifice.

10. The apparatus of claim 8, wherein said cylindrical weight defines a first recess at the first end and a second recess at the second end, such that when the base is held in the first recess the needle of said weighted lancet protrudes from the central opening of the platform at a first depth, and when the base is held in the second recess, the needle of said weighted lancet protrudes from the central opening of the platform at a second depth, greater than the first depth.

11. A method for drawing blood which comprises the following steps:

providing an apparatus for drawing blood which comprises a guide having a first end and a second end and a weighted lancet shaped to slide freely in the guide and to protrude from the first end, said weighted lancet comprising a skin piercing element and a metal weight secured to the skin piercing element;

positioning said weighted lancet at the second end of said guide;

holding said guide between a first finger at the first end and a second finger at the second end, such that the second end is disposed at a lower level than the first end; and inverting said guide such that the first end is disposed at a lower level than the second end, and inertial forces on the said weighted lancet cause said weighted lancet to travel in free fall from the second end to the first end and to pierce the first finger such that a drop of blood may be drawn.

12. A lancet for drawing blood comprising:

a handle, defining an outer end section, a base section, and an external shoulder between the outer end section and the base section;

said base section defining an extreme end portion of said handle, and disposed inwardly with respect to the external shoulder of said handle; and a needle, disposed centrally within said handle and protruding from the outer end of said handle, opposite said base section;

said base section defining a longitudinal axis and a maximum cross-sectional dimension, wherein said outer end section defines a cross-sectional dimension greater than the maximum cross-sectional dimension of the base section, and wherein said needle is aligned with the longitudinal axis.

13. The lancet of claim 12 wherein said handle defines an arcuate surface.

14. The apparatus of claim 8 wherein the mass of the weight is no less than about 0.9 oz.

* * * * *